US011628129B2

(12) United States Patent
Garner et al.

(10) Patent No.: US 11,628,129 B2
(45) Date of Patent: Apr. 18, 2023

(54) METHODS AND COMPOUNDS FOR INCREASING VIRUCIDAL EFFICACY IN HYDROALCOHOLIC SYSTEMS (71) Applicant: GOJO Industries, Inc., Akron, OH (US)

(72) Inventors: Dewain Keith Garner, Copley, OH (US); Rachel Anne Leslie, Akron, OH (US); Anne Matsuda, Bailly Romainvilliers (FR); Magali Moreau, Lesigny (FR)

(73) Assignee: GOJO Industries, Inc., Akron, OH (US)

( * ) Notice: Subject to any disclaimer, the term of this patent is extended or adjusted under 35 U.S.C. 154(b) by 0 days.

(21) Appl. No.: 16/500,241

(22) PCT Filed: Apr. 4, 2017

(86) PCT No.: PCT/IB2017/000493
§ 371 (c)(1),
(2) Date: Oct. 2, 2019

(87) PCT Pub. No.: WO2018/185508
PCT Pub. Date: Oct. 11, 2018

(65) Prior Publication Data
US 2020/0179250 A1    Jun. 11, 2020

(51) Int. Cl.
*A61K 8/34* (2006.01)
*A61P 31/14* (2006.01)
*A61K 8/04* (2006.01)
*A61K 8/41* (2006.01)
*A61K 8/81* (2006.01)
*A61Q 17/00* (2006.01)

(52) U.S. Cl.
CPC .............. *A61K 8/34* (2013.01); *A61K 8/042* (2013.01); *A61K 8/411* (2013.01); *A61K 8/8147* (2013.01); *A61P 31/14* (2018.01); *A61Q 17/005* (2013.01)

(58) Field of Classification Search
None
See application file for complete search history.

(56) References Cited

U.S. PATENT DOCUMENTS

| | | |
|---|---|---|
| 3,069,319 A | 12/1962 | Stearns |
| 3,954,960 A | 5/1976 | Valan |
| 4,692,277 A | 9/1987 | Siklosi |
| 4,933,177 A | 6/1990 | Grollier et al. |
| 4,956,170 A | 9/1990 | Lee |
| 4,961,921 A | 10/1990 | Chuang et al. |
| 5,167,950 A | 12/1992 | Lins |
| 5,266,598 A | 11/1993 | Ninomiya et al. |
| 5,340,570 A | 8/1994 | Wong et al. |
| 5,714,135 A | 2/1998 | Lee et al. |
| 5,968,204 A | 10/1999 | Wise |
| 5,985,294 A | 11/1999 | Peffly |
| 6,022,551 A | 2/2000 | Jampani |
| 6,080,417 A | 6/2000 | Kramer et al. |
| 6,096,297 A | 8/2000 | Jones et al. |
| 6,096,349 A | 8/2000 | Petri et al. |
| 6,123,953 A | 9/2000 | Greff |
| 6,183,766 B1 | 2/2001 | Sine |
| 6,221,922 B1 | 4/2001 | Policello et al. |
| 6,228,385 B1 | 5/2001 | Shick |
| 6,238,682 B1 | 5/2001 | Klofta et al. |
| 6,344,218 B1 | 2/2002 | Dodd et al. |
| 6,383,997 B1 | 5/2002 | McManus |
| 6,423,329 B1 | 7/2002 | Sine et al. |
| 6,562,360 B2 | 5/2003 | Scholz et al. |
| 6,617,294 B2 | 9/2003 | Narula et al. |
| 6,623,744 B2 | 9/2003 | Amus et al. |
| 6,723,689 B1 | 4/2004 | Hoang et al. |
| 6,793,914 B2 | 9/2004 | Clarkson et al. |
| 6,846,352 B2 | 1/2005 | Yatake |
| 7,199,090 B2 | 4/2007 | Koivisto et al. |
| 7,247,295 B2 | 7/2007 | Schmaus et al. |
| 7,384,646 B2 | 6/2008 | Koybayashi et al. |
| 7,537,652 B2 | 5/2009 | Koganehira et al. |
| 7,566,460 B2 | 7/2009 | Asmus et al. |
| 7,582,681 B2 | 9/2009 | Schmaus et al. |

(Continued)

FOREIGN PATENT DOCUMENTS

| | | |
|---|---|---|
| EP | 0796610 A1 | 9/1997 |
| EP | 1668105 B1 | 6/2006 |
| EP | 1764135 A1 | 3/2007 |
| EP | 1769824 A1 | 4/2007 |
| EP | 1967576 A1 | 9/2009 |
| FR | 2771632 A1 | 6/1999 |
| FR | 2857222 A1 | 1/2005 |
| JP | 11322591 A | 11/1999 |
| JP | 2004352688 A | 12/2004 |
| JP | 2005526036 A | 9/2005 |
| JP | 2006273719 A | 10/2006 |
| JP | 2007145750 A | 6/2007 |
| JP | 2007532542 A | 11/2007 |
| JP | 2009517152 A | 4/2009 |
| KR | 1020080108972 A | 12/2008 |

(Continued)

OTHER PUBLICATIONS

Lens et al., A scientific study that proves alcohol hand sanitiser is more efficacious when dispensed onto the hands as foam rather than as gel, Canadian Journal of Infection Control . Spring2011, vol. 26 Issue 1, pp. 21-25.

(Continued)

*Primary Examiner* — Melissa L Fisher
(74) *Attorney, Agent, or Firm* — Calfee, Halter & Griswold LLP (57) ABSTRACT

A topical sanitizing composition for reducing the concentration of non-enveloped viruses on the skin is provided. The topical sanitizing composition includes one or more pH adjusters, at least one carbomer, and at least about 50 wt. % of one or more $C_{1-8}$ alcohols. The sanitizing composition with pH adjuster and carbomer is able to achieve at least a 3.0 log reduction in the concentration of the non-enveloped virus and in some cases passes the EN 14476 standard.

21 Claims, 2 Drawing Sheets

(56) References Cited

U.S. PATENT DOCUMENTS

| | | | |
|---|---|---|---|
| 7,632,871 B2 | 12/2009 | Kobayashi et al. | |
| 7,651,990 B2 | 1/2010 | Asmus | |
| 7,670,615 B2 | 3/2010 | Veeger et al. | |
| 7,824,665 B2 | 11/2010 | Miyamoto et al. | |
| 7,985,773 B2 | 7/2011 | Greten et al. | |
| 8,062,649 B2 | 11/2011 | Asmus et al. | |
| 8,304,375 B1 | 11/2012 | Woff et al. | |
| 8,309,111 B2 | 11/2012 | Fernandez de Castro et al. | |
| 8,329,758 B2 | 12/2012 | Ali et al. | |
| 8,333,954 B2 | 12/2012 | Seidling et al. | |
| 8,431,142 B2 | 4/2013 | Redmond et al. | |
| 8,697,140 B2 | 4/2014 | Arndt et al. | |
| 8,840,911 B2 | 9/2014 | Flugge-Berendes et al. | |
| 9,023,374 B2 | 5/2015 | Touitou | |
| 9,089,129 B2 | 7/2015 | Heisig et al. | |
| 9,114,156 B2 | 8/2015 | Childers | |
| 9,161,531 B2 | 10/2015 | Korb et al. | |
| 9,212,987 B2 | 12/2015 | Copeland et al. | |
| 9,381,150 B2 | 7/2016 | Cunningham et al. | |
| 9,402,393 B2 | 8/2016 | Macinga et al. | |
| 9,414,586 B2 | 8/2016 | Wegner et al. | |
| 9,426,981 B2 | 8/2016 | Hurtmanns et al. | |
| 9,439,841 B2 | 9/2016 | Wegner et al. | |
| 9,707,162 B2 | 7/2017 | De Szalay | |
| 9,962,323 B2 | 5/2018 | Wegner et al. | |
| 10,004,227 B2 | 6/2018 | Macinga et al. | |
| 10,070,644 B2 | 9/2018 | Kritzler et al. | |
| 2004/0228820 A1 | 11/2004 | Elliott et al. | |
| 2005/0222276 A1 | 10/2005 | Schmaus et al. | |
| 2005/0228032 A1 | 10/2005 | Merianos et al. | |
| 2006/0205619 A1* | 9/2006 | Mayhall | A61K 8/416 510/130 |
| 2007/0059331 A1 | 3/2007 | Schmaus et al. | |
| 2007/0065383 A1 | 3/2007 | Fernandez de Castro | |
| 2007/0065385 A1 | 3/2007 | Porter | |
| 2007/0082039 A1 | 4/2007 | Jones, Jr. et al. | |
| 2007/0138208 A1 | 6/2007 | Scholz et al. | |
| 2007/0148101 A1 | 6/2007 | Synder et al. | |
| 2007/0184013 A1 | 8/2007 | Synder et al. | |
| 2007/0185216 A1 | 8/2007 | Synder et al. | |
| 2007/0197704 A1 | 8/2007 | Walter et al. | |
| 2007/0265352 A1 | 11/2007 | Roeding et al. | |
| 2008/0293825 A1 | 11/2008 | Littau et al. | |
| 2008/0311053 A1 | 12/2008 | Curtis | |
| 2009/0004122 A1 | 1/2009 | Modak et al. | |
| 2009/0018213 A1 | 1/2009 | Synder et al. | |
| 2009/0082472 A1 | 3/2009 | Peters | |
| 2009/0175806 A1 | 7/2009 | Modak et al. | |
| 2009/0227675 A1 | 9/2009 | Lindstrom et al. | |
| 2009/0232860 A1 | 9/2009 | Larson et al. | |
| 2009/0238787 A1 | 9/2009 | Finke et al. | |
| 2010/0068161 A1 | 3/2010 | Todary | |
| 2010/0204323 A1* | 8/2010 | Theiler | A01N 37/36 514/547 |
| 2010/0317743 A1 | 12/2010 | Macinga et al. | |
| 2012/0034314 A1 | 2/2012 | Levison et al. | |
| 2012/0087967 A1 | 4/2012 | Crossley et al. | |
| 2012/0129950 A1 | 5/2012 | Macinga et al. | |
| 2012/0184626 A1 | 7/2012 | Guerra-Vega et al. | |
| 2013/0210929 A1 | 8/2013 | Zhu | |
| 2013/0280312 A1 | 10/2013 | De Szalay | |
| 2014/0024711 A1 | 1/2014 | Hedbom et al. | |
| 2015/0258003 A1 | 9/2015 | Copeland et al. | |
| 2015/0366784 A1 | 12/2015 | Ramirez et al. | |
| 2016/0374958 A1 | 12/2016 | Anastassov et al. | |
| 2017/0181429 A1 | 6/2017 | Luciow et al. | |
| 2017/0281695 A1 | 10/2017 | Gantz et al. | |
| 2017/0281718 A1 | 10/2017 | Tian et al. | |
| 2018/0140545 A1 | 5/2018 | Tian et al. | |
| 2018/0256462 A1 | 9/2018 | Grascha et al. | |
| 2018/0311127 A1 | 11/2018 | Padyachi et al. | |
| 2019/0069540 A1 | 3/2019 | Hillman et al. | |

FOREIGN PATENT DOCUMENTS

| | | |
|---|---|---|
| WO | 9939687 A1 | 8/1999 |
| WO | 9956715 A1 | 11/1999 |
| WO | 93003998 A1 | 1/2003 |
| WO | 2005030917 A1 | 4/2005 |
| WO | 2005102276 A1 | 11/2005 |
| WO | 2006033970 A2 | 3/2006 |
| WO | 2007044032 A2 | 4/2007 |
| WO | 2007063065 A1 | 6/2007 |
| WO | 2007103687 A2 | 9/2007 |
| WO | 2008067028 A2 | 6/2008 |
| WO | 2008132621 A1 | 11/2008 |
| WO | 2008135085 A1 | 11/2008 |
| WO | 2009058802 A2 | 5/2009 |
| WO | 2016210074 A1 | 12/2016 |
| WO | 2018098152 A1 | 12/2016 |
| WO | 2017102850 A1 | 6/2017 |
| WO | 2018185508 A1 | 11/2018 |

OTHER PUBLICATIONS

Phillips, K. Small but Steady M&A Activity Continues, Chemical Week 169.17 (May 16, 2007): 26.

Mandom Corp., "Development of preservative-free (additive-free) cosmetics using the Mandom proprietary technique by exploiting the antibacterial properties of "alkanediol" moisturizing ingredient," News Release, Sep. 14, 2005, 3 pages, downloaded from: https://www.mandom.co.jp/en/release/pdf/2005091401_en.pdf.

Lubrizol, "Formulating Hydroalcoholic Gels with Carbopol Polymers," Technical Data Sheet 255, Oct. 15, 2013, 6 pages.

World Health Organization, "WHO Guidelines on Hand Hygiene in Health Care," Jan. 1, 2009, 270 pages.

* cited by examiner

METHODS AND COMPOUNDS FOR INCREASING VIRUCIDAL EFFICACY IN HYDROALCOHOLIC SYSTEMS

BACKGROUND

Skin disinfecting or sanitizing compositions have become increasingly popular in the health care industry, as well as with the general public, for providing antimicrobial effectiveness without skin irritation. Generally, these skin disinfecting or sanitizing compositions include alcohol which kills a wide array of microorganisms that may be present on the skin, particularly the hands.

Viruses are the cause of some of the most common human diseases including the common cold, chickenpox, and herpes. Some serious diseases, including those responsible for many of the epidemics of modern society such as Ebola, AIDS, and SARS, are also caused by viruses. Viruses are infective agents consisting of a nucleic acid (DNA/RNA) in a protein coating that attach to living organism host cells and replicate by forcing the host cell to copy the virus' genetic material. Because viruses can replicate in the body in spite of the host's defense mechanisms, viruses can cause lifelong, chronic infections. In addition to their devastating ability to cause serious diseases, viruses are also easily transmitted, able to pass through bodily fluids, contaminated food/drink, insects, and physical contact. Certain types of viruses, known as non-enveloped viruses, are particularly challenging to control and kill due to their unique resistance to chemicals and environmental conditions.

Various antiviral medications have been approved by the FDA and are currently being prescribed to control viral infections. These medications include both compounds that target specific viral infections and broad-spectrum antivirals, which are designed to be effective against many types of viruses. Unlike antibiotics, antiviral medications do not destroy the virus, but instead only inhibit their growth and development.

High alcohol compositions generally help prevent the transmission of viruses and other pathogens by way of the skin. While these high alcohol compositions are generally effective at reducing pathogens, due to the resistant nature of non-enveloped viruses, alcohol alone is often insufficient to achieve the desired reduction in the most resistant non-enveloped viruses. As such, existing sanitizing compositions have proven ineffective at killing and controlling these non-enveloped viruses. Accordingly, there is a need for a sanitizing composition that is able to kill non-enveloped viruses and increase virucidal efficacy better than existing sanitizing compositions.

SUMMARY

According to some exemplary embodiments, a topical sanitizing composition for reducing the concentration of non-enveloped viruses is provided. An exemplary topical sanitizing composition includes at least one pH adjuster and at least one carbomer, which are present in a weight ratio of at least 0.6. The topical sanitizing composition also includes at least about 50.0 wt. % of one or more $C_{1-8}$ alcohols. Application of the topical sanitizing composition achieves at least a 3.0 log reduction of non-enveloped viruses.

In some exemplary embodiments, the carbomer is a cross-linked acrylic acid copolymer.

In some exemplary embodiments, the pH adjuster contains at least one amine or at least one amide group and can be an alkanolamine or an alkanolamide. The pH adjuster can be selected from one or more of aminomethyl propanol ("AMP"), triethanolamine, and tetrahydroxypropyl ethylenediamine.

In some exemplary embodiments, the non-enveloped virus is a poliovirus or an adenovirus.

In some exemplary embodiments, the pH adjuster and carbomer are present in a weight ratio of at least 0.7, or at least 0.8, or at least 1.0 or at least 1.2.

In some exemplary embodiments, the $C_{1-8}$ alcohol is present in an amount above about 70.0 wt. %, or above about 75.0 wt. %, or above about 77.5 wt. %, or above about 80.0 wt. % and is one or more of methanol, ethanol, propanol, butanol, pentanol, hexanol, and isomers and mixtures thereof. In some exemplary embodiments, the $C_{1-8}$ alcohol is a mixture of ethanol and isopropanol.

In some exemplary embodiments, the topical sanitizing composition contains up to about 20.0 wt. % of a humectant, based on the total weight of the topical sanitizing composition, selected from the group consisting of propylene glycol, hexylene glycol, 1,4-dihydroxyhexane, 1,2,6-hexanetriol, sorbitol, butylene glycol, caprylyl glycol, propanediols, such as methyl propane diol, dipropylene glycol, triethylene glycol, glycerin (glycerol), polyethylene glycols, ethoxydiglycol, polyethylene sorbitol, glycerol caprylate/caprate, and combinations thereof.

In some exemplary embodiments, the topical sanitizing composition contains up to about 20.0 wt. % of one or more plug-preventing additives, based on the total weight of the topical sanitizing composition.

In some exemplary embodiments, the topical sanitizing composition contains up to about 10.0 wt. % of a moisturizing ester, based on the total weight of the topical sanitizing composition selected from the group consisting of selected from the group consisting of cetyl myristate, cetyl myristoleate, and other cetyl esters, tocopheryl acetate, diisopropyl sebacate, isopropyl myristate, and combinations thereof.

In some exemplary embodiments, the topical sanitizing composition is in the form of a clear, thickened, gel, which can have a viscosity from about 500 to about 35,000 cP or from about 500 to about 15,000 cP, or from about 500 to about 10,000 cP.

In some exemplary embodiments, the topical sanitizing composition further comprises one or more carriers, which can be water.

In some exemplary embodiments, the potentiometric pH of the topical sanitizing composition is greater than or equal to 6.1, or greater than or equal to 7.1, or greater than or equal to 8.1.

In another exemplary embodiment, a topical sanitizing composition is provided which comprises at least one pH adjuster and at least one carbomer, which are present in a weight ratio of at least about 0.6. The composition further contains at least about 70.0 wt. % of one or more $C_{1-8}$ alcohols. The topical sanitizing composition passes the European EN 14476 standard.

In another exemplary embodiment, a topical sanitizing composition is provided which comprises at least one pH adjuster and at least one carbomer, which are present in a weight ratio of at least about 0.6. The composition further contains at least about 60.0 wt. % of one or more $C_{1-8}$ alcohols. The topical sanitizing composition reduces the concentration of non-enveloped viruses by a statistically significant amount, as compared to an otherwise identical topical composition without a pH adjuster and carbomer weight ratio of at least about 0.6.

In another exemplary embodiment, a skin treatment method for reducing the concentration of non-enveloped viruses is provided is provided. The methodology includes applying a topical sanitizing composition to a skin surface, wherein the topical sanitizing composition comprises at least one pH adjuster and at least one carbomer in a weight ratio of at least about 0.6. The topical composition also includes at least about 50.0 wt. % of one or more $C_{1-8}$ alcohols. Application of the topical sanitizing composition achieves at least a 3.0 log reduction of non-enveloped viruses.

DETAILED DESCRIPTION

Unless otherwise defined, all technical and scientific terms used herein have the same meaning as commonly understood by one of ordinary skill in the art to which this application pertains. Although other methods and materials similar or equivalent to those described herein may be used in the practice or testing of the exemplary embodiments, exemplary suitable methods and materials are described below. In case of conflict, the definitions included in the present specification will control. In addition, the materials, methods, and examples are illustrative only and not intended to be limiting of the general inventive concepts.

The terminology as set forth herein is for description of the exemplary embodiments only and should not be construed as limiting the application as a whole. Unless otherwise specified, "a," "an," "the," and "at least one" are used interchangeably. Furthermore, as used in the description of the application and the appended claims, the singular forms "a," "an," and "the" are inclusive of their plural forms, unless contradicted by the context surrounding such.

The phrase "topical composition" means a composition suitable for application directly to a surface, such as the surface of a human or animal body, including skin, and/or other surfaces, such as hair and nails.

The term "potentiometric pH" refers to the value yielded by a probe that measures the electrical potential between a working and reference electrode in a solution and converts the measurement to a pH value based on calibration with solutions of known pH. The meter may be calibrated with standardized aqueous buffers or alternate solutions. However, actual proton activity may vary, particularly when the system is not aqueous.

The phrase "statistically significant" means p<0.05 for a test composition vs. a control that does not contain the active ingredient. The analysis is completed using 1) a T-test (a statistical examination of two population means) when only comparing one test article vs. one control); or 2) an analysis of variance (ANOVA) test when comparing two or more test articles vs. controls.

The phrase "log kill" or "log reduction" refers to a logarithmic reduction of colony forming units (CFUs) on a given location. Logarithm scales are based on a base of 10 raised to a given power (i.e., Log 4 means $10^4$ or 10,000). In terms of reduction, a reduction of 1-log (90%) reduces the CFUs on a particular area from 1,000,000 to 100,000, a reduction of 2-log (99%) reduces the CFUs on a particular area from 1,000,000 to 10,000, a reduction of 3-log (99.9%) reduces the CFUs on a particular area from 1,000,000 to 1,000, and a reduction of 4-log (99.99%) reduces the CFUs on a particular area from 1,000,000 to 100.

The general inventive concepts relate to a topical composition that contains a polymer or oligomer. The polymer can be a natural or synthetic polymer and can be any type of polymer including, but not limited to, a heteropolymer or a homopolymer. The polymer can be an addition polymer or a condensation polymer. The polymer can further be cationic, anionic, non-ionic, or amphoteric and can comprise monomers that, themselves are cationic, anionic, non-ionic, or amphoteric. In some exemplary embodiments, the polymer is a water soluble polymer, that is, when added to water, the polymer dissolves. In some exemplary embodiments, the polymer comprises one or more acrylic acid monomers or other similar monomers.

In some exemplary embodiments, the polymer is a carbomer. A carbomer is a generic term for polymers primarily made from acrylic acid. Generally, carbomers are cross-linked polymers of acrylic acid, that is, they are made of acrylic acid monomers. However, carbomers can also include various other monomers. The carbomer can be any carbomer or mixtures of carbomers. Exemplary carbomers include, but are not limited to, Carbopol® 934, Carbopol® 940, Carbopol® 941, Carbopol® 980, Carbopol® 981, Carbopol® 2984, Carobpol® 5984, Carbopol® Silk 100, Carbopol® ETD 2020, Carbopol® 1342, Carbopol® 1382, Carbopol® Ultrez 10, Carbopol® Ultrez 20, Carbopol® Ultrez 21, and Carbopol® Ultrez 30, all commercially available from Lubrizol Advanced Materials in Cleveland, Ohio. Other exemplary carbomers include Ashland™ 940, Ashland™ 941, Ashland™ 980, and Ashland™ 981, all commercially available from Ashland Chemical in Covington, K. Other suitable carbomers include polyacrylate, acrylates/$C_{10-30}$ alkyl acrylate cross-polymers, copolymers of acrylic acid and alkyl ($C_5$-$C_{10}$) acrylate, copolymers of acrylic acid and maleic anhydride, and mixtures thereof.

In some exemplary embodiments, the polymer is a cationic polymer. Cationic polymers include, but are not limited to, cationic polysaccharides, cationic copolymers of saccharides and synthetic cationic monomers, and synthetic cationic polymers. Synthetic cationic polymers include cationic polyalkylene imines, cationic ethoxy polyalkylene imines, cationic poly[N-[3-(dialkylammonio)alkyl] N'[3-(alkyleneoxyalkylene dialkylammonio)alkyl]urea dichloride], vinyl caprolactam/VP/di alkylaminoalkyl alkylate copolymers, and polyquaternium polymers.

Examples of cationic polymers include chitosan, copolymers of isophorone diisocyanate and PEG-15 cocamine, vinyl caprolactam/VP/dimethylaminoethyl methacrylate copolymer, polyquaternium-4/hydroxypropyl starch copolymer, butylmethacrylate-(2-dimethylaminoethyl)methacrylate-methylmethacrylate-copolymer, guar hydroxypropyl trimonium chloride and dilinoleyl amidopropyl dimethylammonium chloride hydroxypropyl copolymer.

In one or more embodiments, the polyquaternium polymer includes polyquaternium-2, polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-32, polyquaternium-37, polyquaternium-39, polyquaternium-42, polyquaternium-43, polyquaternium-44, polyquaternium-46, polyquaternium-47, polyquaternium-51, polyquaternium-53, polyquaternium-55, polyquaternium-57, polyquaternium-58, polyquaternium-59, polyquaternium-60, polyquaternium-63, polyquaternium-64, polyquaternium-65, polyquatemium-68, or mixtures thereof.

In some exemplary embodiments, the polymer is a thickener or polymer viscosifier. Non-limiting examples of suitable thickeners and polymer viscosifiers include cellulosic thickeners, ammonium acryloyldimethyltaurate/VP copolymer, ammonium acryloyldimethyltaurate/beheneth-25 methylacrylate copolymer, coceth-7, PPG-1-PEG-9 lauryl glycol ether, and PEG-40 hydrogenated castor oil.

In one or more embodiments, the cellulosic thickener includes hydroxyethyl cellulose, hydroxypropyl cellulose, hydroxypropyl methylcellulose, methyl cellulose, carboxymethyl cellulose, and cellulosic ethyl polymers sold by Dow Chemical, such as Methocel®. In some exemplary embodiments the topical sanitizing composition comprises less than about 10.0 weight percent (wt. %) of the polymer, or less than about 5.0 wt. %, or less than about 1.0 wt. %, or less than about 0.5 wt. %, or less than about 0.4 wt. %, or less than about 0.3 wt. %, or less than about 0.25 wt. %, of the polymer, based on the total weight of the topical sanitizing composition. In some exemplary embodiments, the topical composition comprises from about 0.05 to about 0.3 wt. % of the polymer or from about 0.1 to about 0.2 wt. % of the polymer, or from about 0.15 to about 0.3 wt. %, or from about 0.2 to about 0.3 wt. %, based on the total weight of the topical sanitizing composition.

In some exemplary embodiments, the polymer helps to boost efficacy against non-enveloped viruses. In some exemplary embodiments, the polymer also helps to boost efficacy against enveloped viruses. Viruses are microscopic, infectious organisms made generally of a nucleic acid (DNA/RNA) in a protein coating that infect the cells of living organism. Viruses replicate by forcing the host cell to copy the virus' generic material. Viruses are categorized into two types based on the composition of their outer surface structure: enveloped viruses and non-enveloped viruses. Enveloped viruses have a protein coating (often called a capsid) which is further encased with an outer lipid membrane. The lipid membrane includes phospholipids, proteins, and viral glycoproteins. The glycoproteins allow the virus to identify and attach to receptor sites on the host's cell membranes. Generally, enveloped viruses are unable to withstand hot temperatures, acidic environments, or dry conditions.

Conversely, non-enveloped viruses are surrounded only by the protein coating (capsid) which performs the task of attaching to host cells. Unlike enveloped viruses, non-enveloped viruses are typically resistant to harsh environmental conditions such as to wide ranges of heat, dryness, and acidic conditions as well as to other chemical and physical procedures. In fact, non-enveloped viruses can even survive and remain fully active/infectious in some disinfection processes. These characteristics thus make non-enveloped viruses particularly challenging to kill and control.

In some exemplary embodiments, the carbomer is hydrated prior to inclusion in the topical sanitizing composition. Commercially available carbomers are typically supplied as a dry powder of tightly coiled acidic molecules. The dry carbomer can be dispersed in water, which hydrates the carbomer and begins to uncoil the acidic molecules. In some instances, the carbomer is thickened by converting the acidic molecules into salts. This may be achieved by neutralizing or otherwise altering the pH of the carbomer with, for example, a pH adjuster.

The pH adjuster is not particularly limited and can be selected based on the composition of the hydroalcoholic system or, more specifically, the percentage of alcohol in the system. The pH adjuster can be an acid or base and in this way can be used to adjust the pH in either direction (i.e., make the composition more acidic or more basic). In some exemplary embodiments, the pH adjuster is a long chain hydrocarbon with two or more carbon atoms. The hydrocarbon can be branched or straight and can also be cyclic or linear. The hydrocarbon can have any number of various other functional groups including, but not limited to, amines, esters, carboxylic acids, ethers, amides, alkyl halides, alcohols, phenyls, as well as other carbonyl-containing functional groups. The hydrocarbon molecule can be anionic, cationic, or non-ionic.

In some exemplary embodiments, the pH adjuster is a compound that contains at least one basic nitrogen atom with a lone pair of electrons. These compounds are referred to herein as "amine pH adjusters." In other exemplary embodiments, the pH adjuster is an alkanolamine. The amine may be a primary, secondary, or tertiary amine. In addition to an amine group, the pH adjuster can contain various other functional groups including, but not limited to esters, carboxylic acids, ethers, amides, alkyl halides, alcohols, phenyls, as well as other carbonyl-containing functional groups. The pH adjuster may also be an alkanolamide, an inorganic base, an amino acid, including salts, esters, and acyl derivatives thereof. Non-limiting examples of pH adjusters include diisopropanolamine, triisopropanolamine, tetrahydroxypropyl ethylenediamine (Neutrol® TE), commercially available from BASF Care Creations of Florham Park, N.J., aminomethyl propanol (AMP), triethanolamine (TEA), tromethamine, L-arginine, and Ethomeen® C-25, commercially available from AkzoNobel Personal Care of Bridgewater, N.J.

Exemplary pH adjusters further include sodium hydroxide, monoethanolamine, ammonium hydroxide, potassium hydroxide, and dimethyl stearylamine. Other neutralizing agents are also known, such as $HO(C_mH_{2m})_2NH$, where m has the value of from 2 to 3, and aminomethyl propanol, aminomethyl propanediol, and ethoxylated amines, such as PEG-25 cocamine, polyoxyethylene (5) cocamine (PEG-5 cocamine), polyoxyethylene (25) cocamine (PEG-25 cocamine), polyoxyethylene (5) octadecylamine (PEG-5 stearamine), polyoxyethylene (25) octadecylamine (PEG-25 stearamine), polyoxyethylene (5) tallowamine (PEG-5 tallowamine), polyoxyethylene (15) oleylamine (PEG-15 oleylamine), polyethylene (5) soyamine (PEG-5 soyamine), PEG-15 cocamine, and polyoxyethylene (25) soyamine (PEG-15 soyamine). A number of these are also commercially available under the trade name of Ethomeen® AkzoNobel Personal Care of Bridgewater, N.J.

In some exemplary embodiments the pH adjuster is an acidic compound. Exemplary acidic pH adjusters include, but are not limited to, organic acids, such as citric acid, lactic acid, formic acid, acetic acid, proponic acid, butyric acid, caproic acid, oxalic acid, maleic acid, benzoic acid, carbonic acid, and the like.

In some exemplary embodiments, the topical sanitizing composition comprises at least about 0.005 wt. % of the pH adjuster, or at least about 0.01 wt. %, or at least about 0.02 wt. %, or at least about 0.04 wt. %, or at least about 0.05 wt. %, or at least about 0.06 wt. %, or at least about 0.08 wt. %, or at least about 0.1 wt. %, or at least about 0.14 wt. %, or at least about 0.5 wt. %, or at least about 0.7 wt. %, or at least about 1.0 wt. %, or at least about 2.0 wt. % of the pH adjuster, based on the total weight of the topical sanitizing composition. In some exemplary embodiments, the topical sanitizing composition comprises from about 0.01 to about 2.0 wt. % of the pH adjuster, or from about 0.05 to about 1.0 wt. % of the pH adjuster, or from about 0.1 to about 0.7 wt. % of the pH adjuster, or from about 0.2 to about 0.5 wt. %, or from about 0.14 to about 0.36 wt. %, or from about 0.14 to about 0.24 wt. % of the pH adjuster, based on the total weight of the topical sanitizing composition.

In some exemplary embodiments, the combination of particular polymers, such as a carbomer, with a pH adjuster helps boost the skin's efficacy against non-enveloped viruses. Because of the durability and resistance of non-enveloped viruses to environmental conditions and disinfecting processes pH adjusters and carbomers included in ratios below those disclosed herein, are insufficient to produce the desired reduction in non-enveloped viruses. When the pH adjuster is combined with the polymer, such as a carbomer, the ratio of pH adjuster to carbomer must be sufficiently high to produce an effective kill of these non-enveloped viruses. While ratios of pH adjuster and carbomers are frequently discussed herein, it is to be appreciated that any polymer could be used in conjunction with the pH adjuster.

In some exemplary embodiments, the ratio of pH adjuster to carbomer (pH adjuster/carbomer) in the topical composition is at least about 0.05, or at least about 0.1, or at least about 0.5, or at least about 0.6, or at least about 0.7, or at least about 0.8, or at least about 0.95, or at least about 1.0, or at least about 1.2, or at least about 2.0. In some exemplary embodiments, the ratio of pH adjuster to carbomer is from about 0.2 to about 2.0 and in other exemplary embodiments from about 0.5 to about 1.6. In some exemplary embodiments the ratio of pH adjuster to carbomer is from about 0.5 to about 1.2, or from about 0.5 to 1.0, or from about 0.7 to about 1.2, or from about 0.7 to about 1.0.

In some exemplary embodiments, the topical sanitizing composition is used for application to the skin and may be in the form of a skin cleanser, skin sanitizer, skin protectant, a wipe, a salve, a gel, etc. A wide variety of vehicles may be used to deliver the topical composition, such as, for example pads, bandages, patches, sticks, aerosol dispersers, pump sprays, trigger sprays, canisters, foam pumps, wipes, and the like. The topical sanitizing composition may be applied to the skin before, during, or after skin cleaning. In some exemplary embodiments, the topical sanitizing composition is applied after skin cleaning.

In addition to the applications described herein and while the phrase "topical sanitizing composition" is frequently used, the exemplary embodiments described herein can also be used on non-mammalian surfaces, that is, surfaces besides those on the human body. For example, the exemplary embodiments disclosed herein can be used to sanitize or cleanse various surfaces in homes and buildings and as well on building materials and furniture.

In some exemplary embodiments, the topical sanitizing composition is an alcohol based sanitizer comprising an alcohol or combination of alcohols. By alcohol, it is meant any organic compound which has a hydroxyl functional group bonded to a saturated carbon atom. Alcohol has antimicrobial properties and has the ability to kill many forms of bacteria, fungi, and viruses. In some embodiments, the alcohol is a $C_{1-8}$ alcohol, i.e. an alcohol containing 1 to 8 carbon atoms. Such alcohols may be referred to as lower alkanols. Examples of lower alkanols include, but are not limited to, methanol, ethanol, propanol, butanol, pentanol, hexanol, and isomers and mixtures thereof. The alcohol may be either pure alcohol or denatured alcohol. In one or more exemplary embodiments, the alcohol comprises ethanol, propanol, or butanol, or isomers or mixtures thereof. In one or more exemplary embodiments, the alcohol comprises isopropanol. In other exemplary embodiments, the alcohol comprises ethanol. In one or more exemplary embodiment, the topical composition comprises a mixture of alcohols. In one or more exemplary embodiments, the topical composition comprises a mixture of ethanol and isopropanol.

While $C_{1-8}$ alcohols are discussed herein, it is envisioned that longer alcohols (alcohols with more than 8 carbon atoms), or alcohols with various other functional groups would be similarly suitable. For example, in addition to the hydroxyl functional group, the alcohol may further contain esters, carboxylic acids, ethers, amides, amines, alkyl halides, phenyls, as well as other carbonyl-containing functional groups. The alcohol can also be an aliphatic alcohol or an aromatic alcohol.

In some exemplary embodiments, the topical sanitizing composition is an alcohol-water based sanitizer, comprising one or more $C_{1-8}$ alcohols and water. These systems are often referred to as hydroalcoholic systems.

In some exemplary embodiments, the topical sanitizing composition comprises at least about 1.0 wt. % $C_{1-8}$ alcohol, based on the total weight of the topical sanitizing composition. In some exemplary embodiments, the topical sanitizing composition comprises at least about 2.0 wt. % $C_{1-8}$ alcohol, or at least about 10.0 wt. % $C_{1-8}$ alcohol, or at least about 20.0 wt. % $C_{1-8}$ alcohol, or at least about 40.0 wt. % $C_{1-8}$ alcohol, or at least about 50.0 wt. % $C_{1-8}$ alcohol, or at least about 60.0 wt. % $C_{1-8}$ alcohol, or at least about 65.0 wt. % $C_{1-8}$ alcohol, or at least about 70.0 wt. % $C_{1-8}$ alcohol, or at least about 75.0 wt. %, or at least about 77.5 wt. %, or at least about 80.0 wt. % $C_{1-8}$ alcohol, based on the total weight of the topical sanitizing composition. In some exemplary embodiments, the topical sanitizing composition comprises from about 60.0 to about 90.0 wt. % $C_{1-8}$ alcohol or from about 65.0 to about 85.0 wt. % $C_{1-8}$ alcohol, based on the total weight of the topical sanitizing composition. In one exemplary embodiment, the topical sanitizing composition comprises from about 60.0 to about 80.0 wt. % $C_{1-8}$ alcohol, or from about 70.0 to about 80.0 wt. %, or from about 75.0 to about 80.0 wt. %, based on the total weight of the topical sanitizing composition. More or less alcohol may be required in certain instances, depending particularly on other ingredients and/or the amounts thereof employed in the topical sanitizing composition.

In some exemplary embodiments, the topical sanitizing composition comprises one or more carriers. The carrier can be any suitable compound able to effectively deliver and/or transport the topical sanitizing composition. In some exemplary embodiments, the carrier is water or a base cleaner. In other exemplary embodiments, the topical sanitizing composition does not include any carrier and is delivered as a concentrate.

In some exemplary embodiments, the topical sanitizing composition includes water as the carrier in an amount quantum sufficit (q.s.). In some exemplary embodiments, the topical sanitizing composition comprises at least about 1.0 wt. % water, or at least about 10.0 wt. % water, or at least about 20.0 wt. % water, or at least about 30.0 wt. % water, or at least about 40.0 wt. % water, or at least about 50.0 wt. % water, or at least about 60.0 wt. % water, or at least about 70.0 wt. % water, based on the total weight of the topical sanitizing composition. In some exemplary embodiments, the topical sanitizing composition comprises from about 5.0 to about 15 wt. % water, or from about 20.0 to about 30.0 wt. % water, or from about 20.0 to about 24.0 wt. % water, based on the total weight of the topical sanitizing composition. More or less water may be required in certain instances, depending particularly on other ingredients and/or the amounts thereof employed in the topical sanitizing composition.

In some exemplary embodiments, the topical sanitizing composition includes one or more humectants. Examples of humectants include propylene glycol, hexylene glycol, 1,4- dihydroxyhexane, 1,2,6-hexanetriol, sorbitol, butylene glycol, caprylyl glycol, propanediols, such as methyl propane diol, dipropylene glycol, triethylene glycol, glycerin (glycerol), polyethylene glycols, ethoxydiglycol, polyethylene sorbitol, and combinations thereof. Other humectants include glycolic acid, glycolate salts, lactate salts, urea, hydroxyethyl urea, alpha-hydroxy acids, such as lactic acid, sodium pyrrolidone carboxylic acid, hyaluronic acid, chitin, glycerol caprylate/caprate (GCC), and the like. In one exemplary embodiment, the humectant is glycerin. In another exemplary embodiment, the humectant is a mixture of glycerin and caprylyl glycol.

Examples of polyethylene glycol humectants include PEG-4, PEG-6, PEG-7, PEG-8, PEG-9, PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240, and PEG-800.

In some exemplary embodiments, the humectant is included in the topical sanitizing composition in an amount up to about 20.0 wt. %, or up to about 15.0 wt. %, or up to about 12.0 wt. %, or up to about 10.0 wt. %, or up to about 8.0 wt. % or up to about 5.0 wt. %, or up to about 3.0 wt. %, based on the total weight of the topical sanitizing composition. In some exemplary embodiments, the humectant is included in an amount from about 0.001 wt. %, or from about 0.01 wt. %, or from about 0.05 wt. %, or from about 0.1 wt. %, or from about 0.5 wt. %, or from about 0.7 wt. %, or from about 1.0 wt. %, or from about 1.5 wt. %, or from about 2.0 wt. %, based on the total weight of the topical sanitizing composition. In one exemplary embodiment, the humectant is included in an amount from about 0.1 to about 2.0 wt. %, based on the total weight of the topical sanitizing composition.

In some exemplary embodiments, the topical sanitizing composition further comprises a plug-preventing additive. In general, the additive prevents the hydroalcoholic gel from coagulating into solid or semi-solid material that may deposit onto a surface or plug a dispenser nozzle. In some exemplary embodiments, the plug-preventing additive can also, as discussed above, act as the humectant.

In some exemplary embodiments, the plug-preventing additive comprises a hydrocarbon chain with two or more carbon atoms. The hydrocarbon can be branched or straight and can also be cyclic or linear. The hydrocarbon can have any number of various functional groups including, but not limited to, amines, esters, carboxylic acids, ethers, amides, alkyl halides, alcohols, phenyls, as well as other carbonyl-containing functional groups. The hydrocarbon molecule can be anionic, cationic, or non-ionic.

In some exemplary embodiments, the hydrocarbon contains one or more esters. In some exemplary embodiments, the plug-preventing additive comprises a monomeric or polymeric di-ester, tri-ester, tetra-ester, penta-ester, or hexa-ester, or a polymeric monoester. In one or more embodiments, the plug-preventing additive includes one or more of $C_1$-$C_{30}$ alcohol esters of $C_1$-$C_{30}$ carboxylic acids, ethylene glycol monoesters of $C_1$-$C_{30}$ carboxylic acids, ethylene glycol diesters of $C_1$-$C_{30}$ carboxylic acids, propylene glycol monoesters of $C_1$-$C_{30}$ carboxylic acids, propylene glycol diesters of $C_1$-$C_{30}$ carboxylic acids, $C_1$-$C_{30}$ carboxylic acid monoesters and polyesters of polypropylene glycols, $C_1$-$C_{30}$ carboxylic acid monoesters and polyesters of polypropylene glycols, $C_1$-$C_{30}$ carboxylic acid monoesters and polyesters of $C_4$-$C_{20}$ alkyl ethers, $C_1$-$C_{30}$ carboxylic acid monoesters and polyesters of di-$C_8$-$C_{30}$ alkyl ethers, and mixtures thereof.

Non-limiting examples of plug-preventing additives with esters include acetyl tributyl citrate, acetyl triethyl citrate, acetyl triethylhexyl citrate, acetyl trihexyl citrate, butyl benzyl phthalate, butyl phthalyl butyl glycolate, butyroyl trihexyl citrate, dibutyl adipate, dibutyloctyl malate, dibutyl oxalate, dibutyl phthalate, dibutyl sebacate, dicapryl adipate, dicaprylyl/capryl sebacate, diethylene glycol dibenzoate, diethylene glycol diethylhexanoate/diisononanoate, diethylene glycol diisononanoate, diethylene glycol rosinate, diethylhexyl adipate, diethylhexyl phthalate, diethylhexyl sebacate, diethylhexyl succinate, diethylhexyl terephthalate, diethyl oxalate, diethyl phthalate, diethyl sebacate, diethyl succinate, diisoamyl malate, diisobutyl adipate, diisobutyl maleate, diisobutyl oxalate, diisocetyl adipate, diisocetyl dodecanedioate, diisodecyl adipate, diisononyl adipate, diisocetyl adipate, diisooctyl maleate, diisooctyl sebacate, diisopropyl adipate, diisopropyl oxalate, diisopropyl sebacate, diisopropyl dimer dilinoleate, diisostearyl adipate, diisostearyl fumarate, diisostearyl glutarate, diisostearyl malate, diisostearyl sebacate, dimethyl adipate, dimethyl oxalate, dimethyl phthalate, dioctyldodecyl adipate, Dioctyldodecyl Dimer Dilinoleate, Dioctyldodecyl Dodecanedioate, Dioctyldodecyl Fluoroheptyl Citrate, Dioctyldodecyl IPDI, Dioctyldodecyl Lauroyl Glutamate, Dioctyldodecyl Malate, Dioctyldodecyl Sebacate, Dioctyldodecyl Stearoyl Glutamate, dipentaerythrityl hexa $C_{5-9}$ acid esters, dipentaerythrityl hexa $C_{5-10}$ acid esters, dipropyl oxalate, pentaerythrityl tetra $C_{5-9}$ acid esters, pentaerythrityl tetra $C_{5-10}$ acid esters, tributyl citrate, tricaprylyl/capryl trimellitate, triethyl citrate, triethylene glycol dibenzoate, triethylene glycol rosinate, triethylhexyl citrate, triethylhexyl trimellitate, trimethylpentanediyl dibenzoate, trimethyl pentanyl diisobutyrate, polyglyceryl-6 pentacaprylate, polyglyceryl-10 pentahydroxystearate, polyglyceryl-10 pentaisostearate, polyglyceryl-10 pentalaurate, polyglyceryl-10 pentalinoleate, polyglyceryl-5 pentamyristate, polyglyceryl-4 pentaoleate, polyglyceryl-6 pentaoleate, polyglyceryl-10 pentaoleate, polyglyceryl-3 pentaricinoleate, polyglyceryl-6 pentaricinoleate, polyglyceryl-10 pentaricinoleate, polyglyceryl-4 pentastearate, polyglyceryl-6 pentastearate, polyglyceryl-10 pentastearate, sorbeth-20 pentaisostearate, sorbeth-30 pentaisostearate, sorbeth-40 pentaisostearate, sorbeth-50 pentaisostearate, sorbeth-40 pentaoleate, sucrose pentaerucate, and triacetin, combinations thereof. In some exemplary embodiments the hydrocarbon plug-preventing additive is selected from one or more of ispropyl myristate and diisopropyl sebacate.

In some exemplary embodiments, the plug-preventing additive comprises a polymeric ester. The polymeric ester can include one or more ester groups.

In some exemplary embodiments, the polymer chain includes a polyethylene glycol (PEG) chain, a polypropylene glycol (PPG), or a combination thereof. In one or more embodiments, the polymer chain includes up to about 12 PEG units, PPG units, or a combination thereof. In some exemplary embodiments, the polymer chain includes up to about 10 PEG units, PPG units, or a combination thereof. In some exemplary embodiments, the polymer chain includes up to about 8 PEG units, PPG units, or a combination thereof. In some exemplary embodiments, the polyether polymer chain includes from about 1 to about 12 PPG or PEG units, or from about 2 to about 8 PPG or PEG units, or a combination thereof.

In some exemplary embodiments, polymeric ester is one that is represented by the following formula:

wherein $R^1$ is a linear or branched alkyl group having from 1 to 28 carbon atoms, each $R^2$, which may be the same or different, includes a polyether chain having up to about 12 PEG or PPG groups, or a combination thereof, and each $R^3$, which may be the same or different, includes an alkyl or alkylene group having from 1 to about 30 carbon atoms, and wherein each $R^3$ group is attached to $R^2$ via an ether linkage.

In some exemplary embodiments, $R^1$ includes up to about 20 carbon atoms, or up to about 10 carbon atoms, or up to about 8 carbon atoms. In some exemplary embodiments, $R^3$ may be represented by the formula $CH_3(CH_2)_zO—$, wherein z is an integer from 1 to about 21, or from 2 to about 17, or from 3 to about 15.

In some exemplary embodiments, the polymeric ester is represented by the following formula:

wherein $R^4$ includes a linear or branched, alkyl or alkylene group having from 1 to about 22 carbon atoms. In some exemplary embodiments, $R^4$ may be represented by the formula $CH_3(CH_2)_z—$, wherein some exemplary embodiments z is an integer from 1 to about 21, or from 2 to about 17, or from 3 to about 15. In some exemplary embodiments, n is an integer from 1 to about 20, or from 2 to about 10. In some exemplary embodiments x is an integer up to about 12, or up to about 10, or up to about 8, or is zero. In some exemplary embodiments, y is an integer up to about 12, or up to about 10, or up to about 8, or is zero. Examples of polymeric esters further include those that may be represented by the following formula:

wherein $R^1$, $R^2$, and $R^3$ are as described hereinabove.

In some exemplary embodiments, the polymeric esters includes any of the above di-, tri, tetra-, penta-, or hexa-esters modified to include a PPG, PEG, or PPG/PEG polymer chain of the appropriate length. Specific examples include Di-PPG-3-ceteth-4 adipate, Di-PPG-2-myreth-10 adipate, Di-PPG-3-myristyl ether adipate, and PPG-2 myristyl ether propionate. In some exemplary embodiments, a mixture of one or more polymeric esters and one or more monomeric di-, tri-, tetra-, penta-, or hexa-esters may be employed as plug-preventing additives.

In some exemplary embodiments, the plug-preventing comprises one or more diols, which are compounds with two hydroxyl groups. Plug-preventing additives that contain more or less hydroxyl groups (i.e., one hydroxyl group and three or more hydroxyl groups) are also within the purview of the exemplary embodiments disclosed herein. In one or more exemplary embodiments, the diol is a $C_{6-10}$ alkane diol and/or a straight chain $C_{6-10}$ alkane diol. Non-limiting examples of suitable diols include 1,2-hexanediol, 1,2-octanediol (often referred to as caprylyl glycol), 1,9-nonanediol, 1,2-decanediol, 1,10-decanediol, or mixtures and blends thereof. It is envisioned that the diol can contain any other functional groups including, for example, esters, carboxylic acids, ethers, amides, amines, alkyl halides, phenyls, as well as other carbonyl-containing functional groups. In some exemplary embodiments, the plug-preventing agent contains at least one ester and/or at least one amide group. In some exemplary embodiments, the plug-preventing agent is selected from glyceryl caprylate/caprate (GCC) and cocoamide diethanolamine.

If separate from the humectant, the plug-preventing additive may be included in the topical sanitizing composition in an amount up to about 20.0 wt. %, or up to about 15.0 wt. %, or up to about 12.0 wt. %, or up to about 10.0 wt. %, or up to about 8.0 wt. % or up to about 5.0 wt. %, or up to about 3.0 wt. %, based on the total weight of the topical sanitizing composition. In some exemplary embodiments, the plug-preventing agent is included in an amount from about 0.001 wt. %, or from about 0.01 wt. %, or from about 0.05 wt. %, or from about 0.1 wt. %, or from about 0.5 wt. %, or from about 0.7 wt. %, or from about 1.0 wt. %, or from about 1.5 wt. %, or from about 2.0 wt. %, based on the total weight of the topical sanitizing composition. In some exemplary embodiments, the plug-preventing additive is included in an amount from about 0.05 to about 4.0 wt. %, or from about 0.1 to about 1.0 wt. %, or from about 0.15 to about 0.7 wt. %, or from about 0.2 to about 0.7 wt. %, based on the total weight of the topical sanitizing composition.

In some exemplary embodiments, the plug-preventing additive is added to the topical sanitizing composition as a solution or emulsion. That is, the plug-preventing additive can be premixed with a carrier to form a solution or emulsion, with the proviso that the carrier does not deliriously effect the ability of the sanitizing composition to sanitize and kill non-enveloped viruses. Examples of carriers include water, alcohol, glycols such as propylene or ethylene glycol, ketones, linear and/or cyclic hydrocarbons, triglycerides, carbonates, silicones, alkenes, esters such as acetates, benzoates, fatty esters, glycerol esters, ethers, amides, polyethylene glycols and PEG/PPG copolymers, inorganic salt solutions such as saline, and mixtures thereof. It will be understood that, when the plug-preventing additive is premixed to form a plug-preventing additive solution or emulsion, the amount of solution or emulsion that is added to the topical sanitizing composition is selected so that the amount of plug-preventing additive falls within the ranges set forth herein.

In some exemplary embodiments, the topical composition further comprises one or more conditioning or moisturizing esters. Examples of such conditioning or moisturizing esters include cetyl myristate, cetyl myristoleate, and other cetyl esters, diisopropyl sebacate, and isopropyl myristate. In one exemplary embodiment, the moisturizing ester is isopropyl myristate.

In some exemplary embodiments, the moisturizing ester is present in an amount of up to about 10.0 wt. %, or up to about 8.0 wt. %, or up to about 5.0 wt. %, or up to about 3.0 wt. %, or up to about 2.0 wt. %, or up to about 1.0 wt. %, based on the total weight of the topical sanitizing composition. In some exemplary embodiments, the moisturizing ester is present in an amount from about 0.0001 wt. %, or from about 0.0005 wt. %, or from about 0.001 wt. %, or from about 0.005 wt. %, or from about 0.01 wt. %, or from about 0.1 wt. %, or from about 0.25 wt. %, or from about 0.5 wt. %, or from about 1.0 wt. %, based on the total weight of the topical sanitizing composition. In one exemplary embodiment, the moisturizing ester is present in an amount from about 0.0005 to about 0.01 wt. %, based on the total weight of the topical sanitizing composition. In another exemplary embodiment, the moisturizing ester is present in an amount from about 0.001 to about 0.005 wt. %, based on the total weight of the topical sanitizing composition.

In some exemplary embodiments, the topical sanitizing composition includes one or more emulsifying agents. Examples of emulsifying agents include stearyl alcohol, sorbitan oleate trideceth-2, poloxamers, and PEG/PPG-20/6 dimethicone. In some exemplary embodiments, the emulsifying agent is present in an amount of up to about 10.0 wt. %, based on the total weight of the topical sanitizing composition. In other exemplary embodiments, the emulsifying agent is present in an amount of from about 0.1 to about 5.0 wt. %, or from about 0.5 to about 2.0 wt. %, based on the total weight of the topical sanitizing composition.

In some exemplary embodiments, the topical sanitizing composition includes one or more skin-conditioners or emollients. Non-limiting examples of suitable skin conditioners and emollients include aloe, vitamin E, vitamin E acetate (tocopheryl acetate), Vitamin $B_3$ (niacinamide), $C_{6-10}$ alkane diols, coco-caprylate, lactic acid, and urea.

In some exemplary embodiments, the skin-conditioner is included in the topical sanitizing composition in an amount from about 0.0001 to about 1.0 wt. %, in other embodiments, from about 0.0005 to about 0.01 wt. %, based on the total weight of the topical sanitizing composition. In a one exemplary embodiment, the miscellaneous skin conditioner is present in an amount from about 0.1 to about 0.5 wt. %, based on the total weight of the topical sanitizing composition.

In some exemplary embodiments, the topical composition further comprises one or more deposition enhancers. A suitable deposition enhancer works unidirectionally and will allow ingredients within the composition to penetrate deeper into the stratum corneum whilst preventing the loss of materials from the skin. Advantageously, the deposition enhancer provides a cosmetically acceptable skin feel to the formulation.

In some exemplary embodiments, the deposition enhancers include one or more of surfactants, bile salts and derivatives thereof, chelating agents, and sulphoxides.

Some examples of acceptable deposition enhancers include dimethyl sulphoxides (DMSO), DMA, DMF, 1-dodecylazacycloheptan-2-one (azone), pyrrolidones such as 2-Pyrrolidone (2P) and N-Methyl-2-Pyrrolidone (NMP), long-chain fatty acids such as oleic acid and fatty acids with a saturated alkyl chain length of about $C_{10}$-$C_{12}$, essential oils, terpenes, terpenoids, oxazolidinones such as 4-decyloxazolidin-2-one, sodium lauryl sulfate (SLS), sodium laureate, polysorbates, sodium glyacolate, sodium deoxycholate, caprylic acid, EDTA, phospholipids, $C_{12-15}$ Alkyl Benzoate, pentylene glycol, ethoxydiglycol, polysorbate-polyethylenesorbitan-monolaurate, and lecithin.

In one or more exemplary embodiments, the deposition enhancer is a quaternary ammonium compound such as polyquaternium-6, -7, -10, -22, -37, -39, -74 or -101.

In some exemplary embodiments, the deposition enhancer is included in the topical sanitizing composition in an amount from about 0.005 wt. % to about 10.0 wt. %, in other embodiments, from about 0.01 wt. % to about 5.0 wt. %, and in other embodiments, from about 0.05 wt. % to about 3.0 wt. %, based on the total weight of the topical sanitizing composition.

In one or more exemplary embodiments, the deposition enhancer comprises a hydroxy-terminated polyurethane compound chosen from polyolprepolymer-2, polyolprepolymer-14, and polyolprepolymer-15. Polyolprepolymer-2 is sometimes referred to as PPG-12/SMDI copolymer. The polyurethane compound may be present in the topical sanitizing composition in an amount from about 0.005 wt. % to about 5.0 wt. %, in other embodiments, from about 0.01 wt. % to about 3.0 wt. %, and in other embodiments, from about 0.05 wt. % to about 1.0 wt. %, based on the total weight of the topical sanitizing composition.

In some exemplary embodiments, the topical composition further comprises one or more anti-irritants. Anti-irritants reduce signs of inflammation on the skin such as swelling, tenderness, pain, itching, or redness. There are three main types of anti-irritants, all of which are envisioned as being applicable in the exemplary embodiments disclosed herein: (1) compounds that operate by complexing the irritant itself, (2) compounds that react with the skin to block reactive sites preventing the irritant from reacting directly with the skin, and (3) compounds that prevent physical contact between the skin and irritant.

Some exemplary examples of suitable anti-irritants include Aloe Vera, allantoin, anion-cation complexes, aryloxypropionates, azulene, carboxymethyl cellulose, cetyl alcohol, diethyl phthalate, Emcol E607, ethanolamine, glycogen, lanolin, N-(2-Hydroxylthyl) Palmitamide, N-Lauroyl Sarcosinates, Maypon 4C, mineral oils, miranols, Myristyl lactate, polypropylene glycol, polyvinyl pyrrolidone (PVP), tertiary amine oxides, thiodioglycolic acid, and zirconia. In one exemplary embodiment, the anti-irritant is avenanthramides (*Avena sativa* (oat), kernel oil, and glycerin) and niacinamide.

In some exemplary embodiments, the anti-irritant is included in the topical sanitizing composition in an amount up to about 10.0 wt. %, in other embodiments, from about 0.005 wt. % to about 3.0 wt. %, and in other embodiments, from about 0.01 wt. % to about 1.0 wt. %, based on the total weight of the topical sanitizing composition.

In some exemplary embodiments, the topical sanitizing composition further comprises a fragrance. Any scent may be used in the topical sanitizing composition including, but not limited to, any scent classification on a standard fragrance chart, such as floral, oriental, woody, and fresh. Exemplary scents include cinnamon, clove, lavender, peppermint, rosemary, thyme, thieves, lemon, citrus, coconut, apricot, plum, watermelon, ginger, cranberry, and combinations thereof.

In some exemplary embodiments, the fragrance is included in the topical sanitizing composition in an amount from about 0.005 wt. % to about 5.0 wt. %, in other embodiments, from about 0.01 wt. % to about 3.0 wt. %, and in other embodiments, from about 0.05 wt. % to about 1.0 wt. %, based on the total weight of the topical sanitizing composition. The fragrance can be any made of any perfume, essential oil, aroma compounds, fixatives, terpenes, solvents, and the like. In some exemplary embodiments, the essential oils may include, for example, one or more of Limonene, Citrus Aurantium Dulcis (Orange) Peel Oil, Eucalyptus Globulus Leaf Oil, Citrus Grandis (Grapefruit)

Peel Oil, Linalool, Litsea Cubeba Fruit Oil, Lavandula Hybrida Oil, Abies Sibirica Oil, Mentha Citrata Leaf Extract, Coriandrum Sativum (Coriander) Fruit Oil, Piper Nigrum (Pepper) Fruit Oil, and Canarium Luzonicum Gum Nonvolatiles.

The topical sanitizing composition may further comprise a wide range of optional ingredients that do not deleteriously affect the composition's ability to reduce the concentration of non-enveloped viruses. The CTFA International Cosmetic Ingredient Dictionary and Handbook, Eleventh Edition 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the exemplary embodiments disclosed herein. Examples of these functional classes include: abrasives, anti-acne agents, anticaking agents, antioxidants, binders, biological additives, bulking agents, chelating agents, chemical additives; colorants, cosmetic astringents, cosmetic biocides, denaturants, drug astringents, emulsifiers, external analgesics, film formers, fragrance components, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, keratolytics, topical active ingredients, and the like.

As the topical sanitizing composition is only semi-aqueous, the pH value obtained is an potentiometric pH and the actual proton activity may vary. The potentiometric pH of the topical sanitizing composition is not particularly limited. In some exemplary embodiments, the potentiometric pH can range from about 1.0 to about 12.0. In some exemplary embodiments, the potentiometric pH ranges from about 3.0 to about 11.0, or from about 4.0 to about 10.5, or from about 5.0 to about 10.0, or about 6.0 to about 10.0, or about 6.5 to about 9.5, or from about 6.7 to about 9.2, or from about 6.9 to about 9.0, or from about 7.1 to about 8.8, or from about 7.3 to about 8.6, or from about 7.5 to about 8.3. In some exemplary embodiments, the potentiometric pH ranges from about 7.0 to about 9.3, or from about 7.85 to about 9.4. In some exemplary embodiments, the potentiometric pH of the topical sanitizing composition is greater than or equal to 6.1, greater than or equal to 6.2, greater than or equal to 6.3, greater than or equal to 6.4, greater than or equal to 6.5, greater than or equal to 6.6, greater than or equal to 6.7, greater than or equal to 6.8, greater than or equal to 6.9, greater than or equal to 7.0, greater than or equal to 7.1, greater than or equal to 7.2, greater than or equal to 7.3, greater than or equal to 7.4, greater than or equal to 7.5, greater than or equal to 7.6, greater than or equal to 7.7, greater than or equal to 7.8, greater than or equal to 7.9, greater than or equal to 8.0, greater than or equal to 8.1, greater than or equal to 8.2, greater than or equal to 8.3, greater than or equal to 8.4, greater than or equal to 8.5, greater than or equal to 8.6, greater than or equal to 8.7, greater than or equal to 8.8.

The form of the topical sanitizing composition of the exemplary embodiments disclosed herein is not particularly limited. In one or more exemplary embodiments, the topical sanitizing composition is formulated as a gel composition, a sprayable liquid, a rinse, or may be applied to a wipe. If formulated as a gel composition, it is advantageous that the gel is clear as opposed to a gel that is cloudy or hazy.

In some exemplary embodiments, the gel composition has a viscosity range of from about 1.0 to about 65,000 centipoise (cP). In one embodiment, the viscosity of the gel is from about 500 to about 35,000 cP, in another exemplary embodiment, the viscosity is from about 500 to about 15,000 cP, in another exemplary embodiment, the viscosity is from about 750 to about 15,000 cP, in another exemplary embodiment, the viscosity is from about 500 to about 10,000 cP, in another exemplary embodiment, the viscosity is from about 1,000 to about 10,000 cP, and in still another exemplary embodiment, the viscosity is from about 2,000 to about 5,000 cP. The viscosity is measured by a Brookfield RV Viscometer using RV and/or LV Spindles at 22° C. +/−3° C.

As will be appreciated by one of skill in the art, the effective amount of thickener will vary depending upon a number of factors, including the amount of alcohol and other ingredients in the gel composition. In one or more embodiments, an effective amount of thickener is at least about 0.01 wt. %, based on the total weight of the gel composition. In other embodiments, the effective amount is at least about 0.02 wt. %, or at least about 0.05 wt. %, or at least about 0.1 wt. %, based on the total weight of the gel composition. In some exemplary embodiments, the effective amount of thickener is at least about 0.5 wt. %, or at least about 0.75 wt. %, based on the total weight of the gel composition. In some exemplary embodiments, topical sanitizing composition comprises up to about 10.0 wt. % of a polymeric thickener, based on the total weight of the topical sanitizing composition. In some exemplary embodiments, the amount of thickener is from about 0.01 to about 1.0 wt. %, or from about 0.02 to about 0.4 wt. %, or from about 0.05 to about 0.3 wt. %, based on the total weight of the gel composition. In other exemplary embodiments, the thickener is included from about 0.1 to about 10.0 wt. %, or from about 0.5% to about 5.0 wt. %, or from about 0.75 to about 2.0 wt. %, based on the total weight of the gel composition.

The topical sanitizing compositions may be dispensed by any type of dispenser typically used for liquids, gels, or foam products, for example pump dispensers. A wide variety of pumps are suitable. The pumps may be affixed to bottles or other free-standing containers. The pumps may be incorporated into wall-mounted dispensers. The pumps may be activated manually by hand or foot pump, or may be automatically activated. Useful dispensers include those available from GOJO Industries under the designations NXT®, TFXC™, DPX™, FMX™, ADX™, LTX™, and CXT™ as well as traditional bag-in-box dispensers. Examples of dispensers are described in U.S. Pat. Nos. 5,265,772, 5,944,227, 6,877,642, 7,028,861, 7,611,030, 7,621,426, 8,740,019, 8,991,657, 9,027,790, 9,073,685, 9,101,250, and 9,204,767, all of which are incorporated herein by reference. In one or more embodiments, the dispenser includes an outlet such as a nozzle, through which the composition is dispensed. In some exemplary embodiments, the topical sanitizing composition is used in dispensers that employ foaming pumps, which combine ambient air or an inert gas and the composition in a mixing chamber and pass the mixture through a mesh screen.

In one or more embodiments, the topical sanitizing composition is integrated into wipe composition. Wipe compositions in accordance with the exemplary embodiments discussed herein, include at least one alcohol, a $C_{1-10}$ alkanediol enhancer, and are applied to a wipe substrate. In some exemplary embodiments, the wipe composition is alcohol-free.

Wipe substrates used in antimicrobial wipes are further described in U.S. Pat. Nos. 5,686,088, 6,410,499, 6,436,892, 6,495,508, 6,844,308, 9,096,821, which are incorporated herein by reference. In one or more embodiments, the wipe may comprise a laminate formed by spunbonding/meltblowing/spunbonding (SMS). Generally, an SMS material contains a meltblown web sandwiched between two exteriors spunbond webs. SMS materials are further described in U.S. Pat. Nos. 4,041,203, 5,169,706, 5,464,688, and 4,766,029, which are incorporated herein by reference and are commercially available, for example from Kimberly-Clark Corporation under marks such as Spunguard 7 and Evolution 7. The SMS laminate may be treated or untreated. The wipes according to the exemplary embodiments described herein can be hand wipes, face wipes, industrial wipes, household wipes, and other similar wipes.

In some exemplary embodiments, the topical sanitizing composition includes the following:

TABLE 1

| Ingredient | Wt. % |
|---|---|
| Water | 5.0-15.0 |
| Carbomer | 0.10-0.5 |
| Ethanol | 70.0-95.0 |
| Isopropanol | 2.0-5.0 |
| pH adjuster | 0.10-0.50 |
| pH adjuster/carbomer | 0.7-1.5 |

TABLE 2

| Ingredient | Wt. % |
|---|---|
| Water | 8.0-11.0 |
| Carbomer | 0.15-0.30 |
| Ethanol | 80.0-90.0 |
| Isopropanol | 3.5-4.5 |
| pH adjuster | 0.20-0.3 |
| pH adjuster/carbomer | 0.9-1.3 |

TABLE 3

| Ingredient | Wt. % |
|---|---|
| Water | 5.0-15.0 |
| Carbomer | 0.10-0.5 |
| Ethanol | 70.0-95.0 |
| Isopropanol | 2.0-5.0 |
| pH adjuster | 0.10-0.50 |
| pH adjuster/carbomer | 0.6-1.5 |

TABLE 4

| Ingredient | Wt. % |
|---|---|
| Water | 9.0-11.0 |
| Carbomer | 0.20-0.40 |
| Ethanol | 80.0-90.0 |
| Isopropanol | 3.0-4.0 |
| pH adjuster | 0.15-0.40 |
| pH adjuster/carbomer | 0.6-1.2 |

In some exemplary embodiments, a topical sanitizing composition with at least one carbomer, at least one amine pH adjuster, and at least about 50.0 wt. % of one or more $C_{1-8}$ alcohols is able to pass the current version of the EN 14476 test standard approved Jul. 5, 2013, as amended on Aug. 31, 2015 ("EN 14476"). EN 14476 is a European test standard, approved by The European Committee for Standardization (CEN), that provides the minimum requirements for virucidal activity of chemical disinfectants and antiseptic products. The standard applies to products used in the medical field, in the fields of hygienic hand-rub, hygienic hand-wash, instrument disinfection by immersion, surface disinfection by wiping, spraying, flooding, etc. or textile disinfection. The EN 14476 standard requires that a chemical disinfectant for hand hygiene achieve at least a 4.0 log reduction in virus titer for poliovirus, adenovirus, and murine norovirus when tested in accordance the test methods described in EN 14476.

In some exemplary embodiments, a topical sanitizing composition with at least one carbomer, at least one amine pH adjuster, and at least about 70.0 wt. % of one or more $C_{1-8}$ alcohols decreases the concentration of non-enveloped viruses, such as the poliovirus. Poliovirus, a non-enveloped virus, is the causative agent of poliomyelitis (polio), a highly infectious viral disease which is transmitted horizontally. Three serotypes of poliovirus have been identified: PV1, PV2, and PV3, each exhibiting a different capsid protein. Complications from polio include muscle weakness, paralysis, and in some cases, death. EN 14476 uses poliovirus as a standard in measuring virucidal activity because it is a well-studied non-enveloped virus and similar in chemical resistance to a wide variety of other human viruses. In some exemplary embodiments, a topical sanitizing composition comprising a ratio of amine pH adjuster/carbomer of at least about 0.5 in a hydroalcoholic system with at least about 70.0 wt. % of one or more $C_{1-8}$ alcohols is able to achieve a poliovirus log kill of at least 1.88, or at least 3.13, or at least 3.38, or at least 3.88, or at least 4.13. In some exemplary embodiments, the topical sanitizing composition reduces the concentration of non-enveloped viruses, such as the poliovirus by a statistically significant amount and in other exemplary embodiments, passes the EN 14476 standard for non-enveloped virus concentration.

In some exemplary embodiments, a topical sanitizing composition with at least one carbomer, at least one amine pH adjuster, and at least about 50 wt. % of one or more $C_{1-8}$ alcohols decreases the concentration of non-enveloped viruses, such as the adenovirus. Adenovirus is a non-enveloped virus that can infect multiple organ systems and is endemic throughout the year. The adenovirus can enter the human body through any number of different points and the site of entry typically determines the symptoms. For example, adenovirus entry through droplet inhalation generally causes respiratory tract infection while fecal-oral transmission generally causes gastrointestinal infection. EN 14476 uses adenovirus as a standard in measuring virucidal activity because it is a well-studied non-enveloped virus and similar in chemical resistance to a wide variety of other human viruses. In some exemplary embodiments, a topical sanitizing composition comprising a ratio of amine pH adjuster/carbomer of at least about 0.5 in a hydroalcoholic system is able to achieve an adenovirus log kill of at least 0.75, or at least 1.63, or at least 5.13. In some exemplary embodiments, the topical sanitizing composition reduces the concentration of non-enveloped viruses, such as the adenovirus by a statistically significant amount and in other exemplary embodiments, passes the EN 14476 standard for non-enveloped virus concentration.

EXAMPLES

The following examples are included for purposes of illustration and are not intended to limit the scope of the methods described herein.

The following Examples are the result of studies carried out according to the test methods set forth in EN 14476. For detailed explanations of these methods and tests see NF EN 14476 publication, September 2013 as amended August 2015, available under license from ANFOR—Norm'Info of Rue Francis de Pressense, France, the entirety of which is incorporated herein by reference.

Example 1

Eleven samples were prepared according to the compositions in Table 5 were tested for their ability to reduce the concentration of poliovirus according to the EN 14476 test method. Also added to the samples in Table 5 were glycerin, in an amount up to about 20.0 wt. %, based on the total weight of the topical sanitizing composition and isopropyl myristate, in an amount up to about 10.0 wt. %, based on the total weight of the topical sanitizing composition. The pH adjusters used included either AMP or Neutrol® TE, which is tetrahydroxypropyl ethylenediamine.

TABLE 5

| Comp. # | Ethanol (wt. %) | Isopropanol (wt. %) | Carbomer (wt. %) | AMP/ Carbomer Ratio | AMP (wt. %) | Neutrol ® TE/ Carbomer Ratio | Neutrol ® TE (wt. %) | Viscosity (cP) | Polio Log Reduction |
|---|---|---|---|---|---|---|---|---|---|
| 1 | 75 | 4 | 0.3 | 0.7 | 0.21 | 0 | 0 | 4810 | 3.38 |
| 2 | 80 | 4 | 0.2 | 0.7 | 0.14 | 0 | 0 | 2870 | 3.88 |
| 3 | 75 | 4 | 0.3 | 1.2 | 0.36 | 0 | 0 | 4520 | 4.13 |
| 4 | 75 | 4 | 0.2 | 0.7 | 0.14 | 0 | 0 | 3600 | 3.13 |
| 5 | 80 | 4 | 0.3 | 0.7 | 0.21 | 0 | 0 | 3210 | 3.88 |
| 6 | 80 | 4 | 0.3 | 1.2 | 0.36 | 0 | 0 | 4340 | 4.13 |
| 7 | 80 | 4 | 0.2 | 1.2 | 0.24 | 0 | 0 | 2460 | 4.13 |
| 8 | 77.5 | 4 | 0.25 | 0.95 | 0.24 | 0 | 0 | 3840 | 4 |
| 9 | 75 | 4 | 0.2 | 1.2 | 0.24 | 0 | 0 | 2050 | 3.75 |
| 10 | 77.5 | 4 | 0.25 | 0 | 0 | 0.5 | 0.125 | 3220 | 1.88 |
| 11 | 77.5 | 4 | 0.25 | 0 | 0 | 1 | 0.25 | 4030 | 3.38 |

Figure 1:
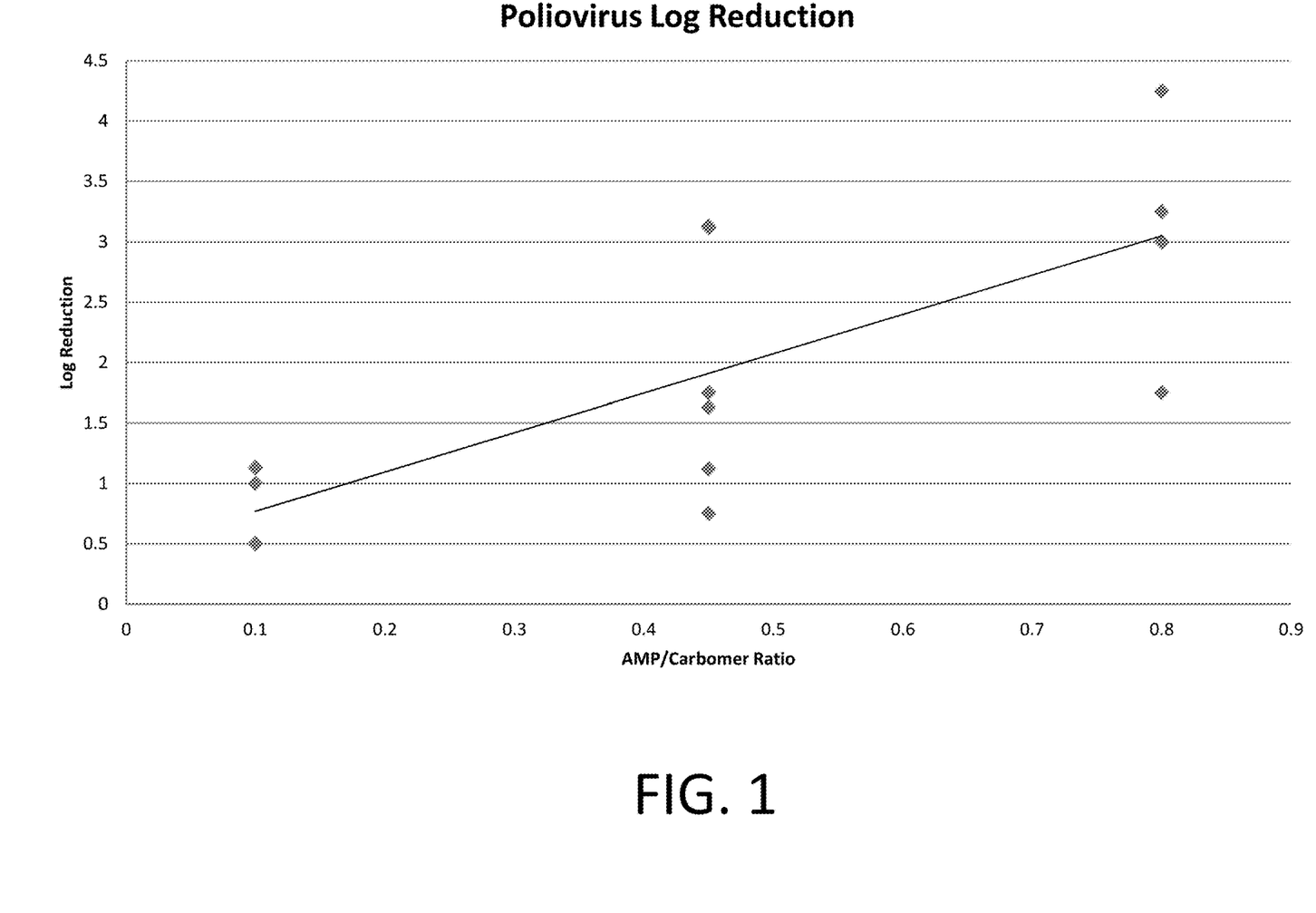
FIG. 1 illustrates an exemplary graph of pH adjuster/carbomer ratio verses poliovirus log reduction.

Preparation of each sample according to Table 5 resulted in a clear gel composition. The results show that compositions with pH adjuster/carbomer ratios above about 0.5 were able to achieve exceptional poliovirus log reductions after a 120 second exposure, including up to a 4.13 log reduction. The results are depicted graphically in FIG. 1, which shows a graph of poliovirus log reduction verses pH adjuster/carbomer ratio.

Example 2

Eleven samples were prepared according to the compositions in Table 6 were tested for their ability to reduce the concentration of adenovirus according to the EN 14476 test method outlined above. Also added to the samples in Table 6 were glycerin, in an amount up to about 20.0 wt. %, based on the total weight of the topical sanitizing composition and isopropyl myristate, in an amount up to about 10.0 wt. %, based on the total weight of the topical sanitizing composition.

TABLE 6

| Comp. # | Ethanol (wt. %) | Isopropanol (wt. %) | Carbomer (wt. %) | AMP/ Carbomer Ratio | AMP (wt. %) | Neutrol ® TE/ Carbomer Ratio | Neutrol ® TE (wt. %) | Viscosity (cP) | Adeno Log Reduction |
|---|---|---|---|---|---|---|---|---|---|
| 12 | 75 | 4 | 0.3 | 0.7 | 0.21 | 0 | 0 | 4810 | 5.13 |
| 13 | 80 | 4 | 0.2 | 0.7 | 0.14 | 0 | 0 | 2870 | 5.13 |
| 14 | 75 | 4 | 0.3 | 1.2 | 0.36 | 0 | 0 | 4520 | 5.13 |
| 15 | 75 | 4 | 0.2 | 0.7 | 0.14 | 0 | 0 | 3600 | 5.13 |
| 16 | 80 | 4 | 0.3 | 0.7 | 0.21 | 0 | 0 | 3210 | 5.13 |
| 17 | 80 | 4 | 0.3 | 1.2 | 0.36 | 0 | 0 | 4340 | 5.13 |
| 18 | 80 | 4 | 0.2 | 1.2 | 0.24 | 0 | 0 | 2460 | 5.13 |
| 19 | 77.5 | 4 | 0.25 | 0.95 | 0.24 | 0 | 0 | 3840 | 5.13 |
| 20 | 75 | 4 | 0.2 | 1.2 | 0.24 | 0 | 0 | 2050 | 5.13 |
| 21 | 77.5 | 4 | 0.25 | 0 | 0 | 0.5 | 0.125 | 3220 | 1.63 |
| 22 | 77.5 | 4 | 0.25 | 0 | 0 | 1 | 0.25 | 4030 | 0.75 |

Figure 2:
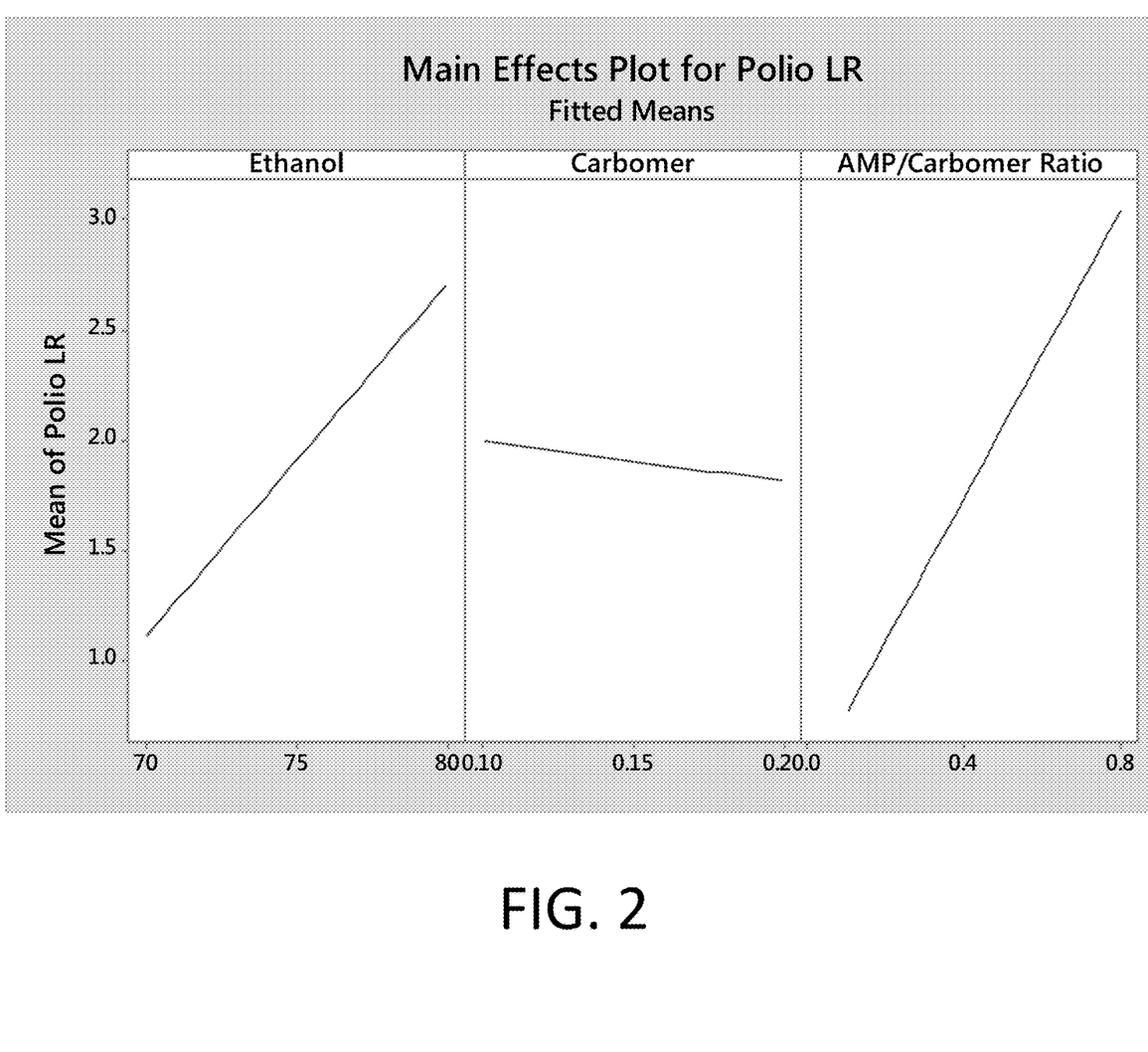
FIG. 2 illustrates an exemplary graph of pH adjuster/carbomer ratio verses adenovirus log reduction.

Preparation of each sample according to Table 6 resulted in a clear gel composition. The results show that compositions with pH adjuster/carbomer ratios above about 0.5 were able to achieve exceptional adenovirus log reductions after a 60 second exposure, including up to a 5.13 log reduction, which is the upper limit of the detection equipment used in analysis of virus activity. The results are depicted graphically in FIG. 2, which shows a graph of adenovirus log reduction verses pH adjuster/carbomer ratio.

Although exemplary embodiments have been described herein, it should be appreciated that many modifications can be made without departing from the spirit and scope of the general inventive concepts. All such modifications are intended to be included within the scope of the exemplary embodiments disclosed herein, which is to be limited only by the following claims.

We claim:

1. A topical sanitizing composition comprising:
   at least one pH adjuster;
   at least one carbomer; and
   greater than 75 wt. % of one or more $C_{1-8}$ alcohols,
   wherein the topical sanitizing composition achieves a log reduction against one or more non-enveloped viruses of at least 3.0,
   wherein the weight ratio of pH adjuster/carbomer in the topical sanitizing composition is at least 0.6/1, and
   wherein the potentiometric pH of the composition is at least 6.1.

2. The topical sanitizing composition of claim 1, wherein the carbomer is a cross-linked polyacrylic acid copolymer.

3. The topical sanitizing composition of claim 1, wherein the pH adjuster contains one or more of an amine group and an amide group.

4. The topical sanitizing composition of claim 1, wherein the pH adjuster is one or more of aminomethyl propanol, triethanolamine, and tetrahydroxypropyl ethylenediamine.

5. The topical sanitizing composition of claim 1, wherein the weight ratio of pH adjuster/carbomer in the topical sanitizing composition is at least 0.7/1.

6. The topical sanitizing composition of claim 1, wherein the $C_{1-8}$ alcohol is one or more of methanol, ethanol, propanol, butanol, pentanol, hexanol, and isomers and mixtures thereof.

7. The topical sanitizing composition of claim 6, wherein the $C_{1-8}$ alcohol is a mixture of ethanol and isopropanol.

8. The topical sanitizing composition of claim 1, wherein the $C_{1-8}$ alcohol is present in an amount of at least 80 wt. %, based on the total weight of the topical sanitizing composition.

9. The topical sanitizing composition of claim 1, wherein the topical sanitizing composition further comprises one or more humectants, selected from the group consisting of propylene glycol, hexylene glycol, 1,4-dihydroxyhexane, 1,2,6-hexanetriol, sorbitol, butylene glycol, caprylyl glycol, propanediol, dipropylene glycol, triethylene glycol, glycerin (glycerol), polyethylene glycol, ethoxydiglycol, polyethylene sorbitol, glycerol caprylate/caprate, and combinations thereof.

10. The topical sanitizing composition of claim 9, wherein the humectant is present in an amount up to 20.0 wt. %, based on the total weight of the topical sanitizing composition.

11. The topical sanitizing composition of claim 1, wherein the topical sanitizing composition further comprises one or more emollients, selected from the group consisting of aloe, vitamin E, vitamin E acetate, Vitamin B3, C6-10 alkane diols, coco-caprylate, lactic acid, urea, and combinations thereof.

12. The topical sanitizing composition of claim 1, wherein the topical sanitizing composition further comprises one or more moisturizing esters, selected from the group consisting of cetyl myristate, cetyl myristoleate, diisopropyl sebacate, isopropyl myristate, and combinations thereof.

13. The topical sanitizing composition of claim 1, wherein the topical sanitizing composition is a clear gel having a viscosity of from 500 to 35,000 cP.

14. The topical sanitizing composition of claim 1, wherein the topical sanitizing composition is a clear gel having a viscosity of from 500 to 15,000 cP.

15. The topical sanitizing composition of claim 1, wherein:
the at least one pH adjuster is present in an amount from 0.01 to 2 wt. %, based on the total weight of the composition; and
the weight ratio of pH adjuster/carbomer in the topical sanitizing composition is at least 1/1.

16. The topical sanitizing composition of claim 1, wherein the at least one carbomer is present in an amount up to 0.5 wt. %, based on the total weight of the composition.

17. The topical sanitizing composition of claim 1, wherein the topical sanitizing composition achieves a log reduction against one or more non-enveloped viruses of at least 4.0.

18. A topical sanitizing composition comprising:
at least one pH adjuster;
an amount up to 0.5 wt. % of at least one carbomer; and
at least 77.5 wt. % of one or more $C_{1-8}$ alcohols,
wherein the weight ratio of pH adjuster/carbomer in the topical sanitizing composition is between 0.6/1 and 2.0/1.

19. The topical sanitizing composition of claim 18, wherein the potentiometric pH of the composition is at least 6.1.

20. The topical sanitizing composition of claim 18, wherein the composition comprises at least 80 wt. % of one or more $C_{1-8}$ alcohols.

21. A method of skin treatment, the method comprising:
applying the topical sanitizing composition of claim 1 to a skin surface.

* * * * *